United States Patent
McGrogan (10) Patent No.: US 11,439,761 B2
(45) Date of Patent: Sep. 13, 2022

(54) CELL DELIVERY SYSTEM AND METHODS OF OPERATION THEREOF

(71) Applicant: SanBio, Inc., Mountain View, CA (US)

(72) Inventor: Michael McGrogan, San Carlos, CA (US)

(73) Assignee: SanBio, Inc., Mountain View, CA (US)

(*) Notice: Subject to any disclaimer, the term of this patent is extended or adjusted under 35 U.S.C. 154(b) by 622 days.

(21) Appl. No.: 16/437,206

(22) Filed: Jun. 11, 2019

(65) Prior Publication Data

US 2019/0290846 A1     Sep. 26, 2019

Related U.S. Application Data

(63) Continuation of application No. PCT/US2017/068288, filed on Dec. 22, 2017.

(60) Provisional application No. 62/439,818, filed on Dec. 28, 2016.

(51) Int. Cl.
| | |
|---|---|
| *A61M 5/315* | (2006.01) |
| *A61M 5/178* | (2006.01) |
| *A61K 35/28* | (2015.01) |
| *A61M 5/31* | (2006.01) |
| *A61M 5/32* | (2006.01) |

(52) U.S. Cl.
CPC ......... *A61M 5/31531* (2013.01); *A61K 35/28* (2013.01); *A61M 5/1782* (2013.01); *A61M 5/315* (2013.01); *A61M 5/3129* (2013.01); *A61M 5/32* (2013.01); *A61M 2209/045* (2013.01); *A61M 2209/088* (2013.01)

(58) Field of Classification Search
CPC ................ A61M 5/31531; A61M 2209/045
See application file for complete search history.

(56) References Cited

U.S. PATENT DOCUMENTS

| | | |
|---|---|---|
| 5,873,879 A | 2/1999 | Figueroa et al. |
| 6,989,271 B2 | 1/2006 | Dezawa et al. |
| 7,137,969 B1 | 11/2006 | Mendez |
| 7,329,241 B2 | 2/2008 | Horvath et al. |
| 7,682,825 B2 | 3/2010 | Dezawa et al. |
| 8,092,792 B2 | 1/2012 | Dezawa et al. |
| 8,133,725 B2 | 3/2012 | Dezawa et al. |
| 8,361,456 B2 | 1/2013 | Dezawa et al. |
| 8,460,269 B2 | 6/2013 | Toma et al. |

(Continued)

FOREIGN PATENT DOCUMENTS

| | | |
|---|---|---|
| CN | 101820861 | 9/2010 |
| EP | 1949904 | 8/2008 |

(Continued)

*Primary Examiner* — Jenna Zhang
(74) *Attorney, Agent, or Firm* — Levine Bagade Han LLP (57) ABSTRACT

A method of preparing a syringe in connection with a therapeutic treatment is disclosed. The method can include removing a plunger of the syringe from a barrel of the syringe, aligning the barrel in a horizontal orientation, filling a lumen of the barrel with a viscous material through an opening at a proximal end of the barrel, and inserting a plunger tip into the lumen to seal the lumen. The method can also include attaching an implantation device to a hub coupled to the barrel at a distal end of the barrel. The method can also include depressing the plunger until the cell suspension fills the implantation device and a droplet of the cell suspension is expelled from a distal tip of the implantation device.

22 Claims, 9 Drawing Sheets

(56) References Cited

U.S. PATENT DOCUMENTS

| | | | |
|---|---|---|---|
| 8,734,382 B2 | 5/2014 | Frankowski et al. | |
| 8,785,190 B2 | 7/2014 | Dao et al. | |
| 8,945,919 B2 | 2/2015 | Mori et al. | |
| 8,969,078 B2 | 3/2015 | Dezawa et al. | |
| 9,326,999 B2 | 5/2016 | Case et al. | |
| 9,381,687 B2 | 7/2016 | Felts et al. | |
| 9,386,972 B2 | 7/2016 | Engh et al. | |
| 9,399,046 B2 | 7/2016 | Dezawa et al. | |
| 9,441,199 B2 | 9/2016 | Dezawa | |
| RE46,382 E | 5/2017 | Dao et al. | |
| 9,655,927 B2 | 5/2017 | Dao et al. | |
| 9,828,593 B2 | 11/2017 | Borlongan et al. | |
| 9,833,226 B2 | 12/2017 | Engh et al. | |
| 9,931,434 B2 | 4/2018 | Bellas et al. | |
| 2002/0077588 A1* | 6/2002 | Schneider | A61M 5/007 604/82 |
| 2002/0192194 A1 | 12/2002 | McGrogan et al. | |
| 2002/0198498 A1* | 12/2002 | Porat | A61M 5/1782 604/187 |
| 2003/0032925 A1* | 2/2003 | Stone | A61M 25/0084 604/191 |
| 2003/0078912 A1* | 4/2003 | Oliver | A61M 31/00 |
| 2003/0211085 A1 | 11/2003 | Sanberg et al. | |
| 2004/0009609 A1 | 1/2004 | Yarborough et al. | |
| 2004/0028656 A1 | 2/2004 | Willing et al. | |
| 2004/0158226 A1 | 8/2004 | Soo Hoo et al. | |
| 2004/0162528 A1 | 8/2004 | Horvath et al. | |
| 2005/0282264 A1 | 12/2005 | Yu et al. | |
| 2005/0283113 A1* | 12/2005 | Brinz | B01L 3/0206 604/82 |
| 2006/0111667 A1* | 5/2006 | Matsuura | A61B 5/150221 604/93.01 |
| 2007/0276323 A9 | 11/2007 | Matsuura et al. | |
| 2008/0103564 A1 | 5/2008 | Burkinshaw et al. | |
| 2008/0108952 A1 | 5/2008 | Horvath et al. | |
| 2008/0113029 A1* | 5/2008 | Fritz | A61K 47/32 424/490 |
| 2008/0132878 A1 | 6/2008 | Kondziolka | |
| 2009/0076477 A1 | 3/2009 | Schneider et al. | |
| 2009/0208464 A1* | 8/2009 | Centeno | A61J 3/00 424/93.7 |
| 2010/0305514 A1* | 12/2010 | Valenti | A61F 9/0017 604/239 |
| 2010/0310529 A1 | 12/2010 | Aizman | |
| 2010/0331767 A1 | 12/2010 | Frankowski et al. | |
| 2011/0136114 A1 | 6/2011 | Case | |
| 2011/0208113 A1 | 8/2011 | Toma et al. | |
| 2013/0197316 A1 | 8/2013 | Engh et al. | |
| 2013/0200549 A1 | 8/2013 | Felts et al. | |
| 2013/0210000 A1 | 8/2013 | Aizman et al. | |
| 2014/0099286 A1 | 4/2014 | Sanberg et al. | |
| 2014/0186316 A1 | 7/2014 | Borlongan et al. | |
| 2014/0219976 A1 | 8/2014 | Case et al. | |
| 2014/0228741 A1 | 8/2014 | Frankowski et al. | |
| 2014/0286918 A1 | 9/2014 | Dao et al. | |
| 2014/0308362 A1 | 10/2014 | Bellas et al. | |
| 2014/0363408 A1 | 12/2014 | Aizman | |
| 2015/0104435 A1 | 4/2015 | Mori et al. | |
| 2015/0197741 A1 | 7/2015 | Borlongan et al. | |
| 2015/0224260 A1 | 8/2015 | Stearns et al. | |
| 2016/0038684 A1 | 2/2016 | Lum et al. | |
| 2016/0263159 A1 | 9/2016 | Dao et al. | |
| 2016/0271181 A1 | 9/2016 | Case et al. | |
| 2016/0287239 A1 | 10/2016 | Engh et al. | |
| 2016/0304835 A1 | 10/2016 | Dezawa et al. | |
| 2017/0151286 A1* | 6/2017 | Kutikov | A01K 67/0271 |

FOREIGN PATENT DOCUMENTS

| | | |
|---|---|---|
| JP | 2002-306596 | 10/2002 |
| JP | 2004-520892 | 7/2004 |
| JP | 2013-541380 | 11/2013 |
| JP | 2014-039836 | 3/2014 |
| JP | 2015-504922 | 2/2015 |
| JP | 2016-515004 | 5/2016 |
| WO | WO 2008/067183 | 6/2008 |
| WO | WO 2015/152721 | 10/2015 |
| WO | WO 2018/125829 | 7/2018 |

* cited by examiner

CELL DELIVERY SYSTEM AND METHODS OF OPERATION THEREOF

CROSS-REFERENCE TO RELATED APPLICATIONS

The present application is a continuation of International Application No. PCT/US2017/068288, filed Dec. 22, 2017, which claims the benefit of U.S. Provisional Application No. 62/439,818, filed Dec. 28, 2016, the contents of which are hereby incorporated by reference in their entirety.

TECHNICAL FIELD

The present disclosure relates generally to the field of cell delivery and, more specifically, to a cell delivery system for delivering high viscosity cell suspensions to a subject in connection with a therapeutic treatment.

BACKGROUND

Stem cell transplantation is a novel therapeutic treatment that relies on the delivery of viable cells to target sites to restore the function of injured tissues. Stem cell transplantation has shown potential in treating neurological diseases and injuries such as stroke, Parkinson's disease, traumatic brain injury, paralysis, and peripheral arterial disease. One common transplantation procedure involves directly injecting stem cells into a patient. Such a procedure often requires the use of a syringe having a small-gauge needle, especially when the target site is small or of limited accessibility. Further, many physicians prefer to use a fine needle in order to minimize damage to the target site.

As such, difficulties can arise when a high concentration of cells needs to be administered to a target site using the precision of a fine needle. For example, certain stem cell treatments involve delivering cells having a concentration greater than 20,000 cells per µL in order to be effective. However, using a needle to draw up cells of such high concentrations can result in blockage of the needle path, which can, in turn, result in cell damage and inconsistent treatment results.

Therefore, a solution is needed that can accurately and reliably deliver high-density cell suspensions for transplantation. Such a solution should reduce cell damage and improve treatment results.

SUMMARY

A method of preparing a syringe in connection with a therapeutic treatment is disclosed. The method can include removing a plunger of the syringe from a barrel of the syringe. The barrel can have a proximal end, a distal end, and a lumen in between the proximal end and the distal end. The method can include aligning the barrel in a horizontal orientation and filling at least part of the lumen of the barrel with a viscous material (e.g., a cell suspension) through an opening at the proximal end. The cell suspension can be a suspension of cells descendant from mesenchymal stem cells transiently-transfected by a polynucleotide encoding a Notch intracellular domain. The lumen can be filled by inserting a pipette tip of a micropipette into the lumen of the barrel through an opening in the proximal end and injecting the cell suspension into the lumen using the micropipette.

The method can also include inserting a plunger tip of the plunger into the lumen to seal the lumen. The plunger tip can comprise a chemically inert polymeric material. The chemically inert polymeric material can include polytetrafluoroethylene (PTFE). The method can further include attaching a cannula to a hub of the syringe. The hub can be coupled to the barrel at the distal end. The method can also include depressing the plunger until the cell suspension fills the cannula and a droplet of the cell suspension is expelled from the distal tip of the cannula.

The method can further include discarding the droplet of the cell suspension expelled from the cannula. The droplet expelled can have a volume between 10 µL and 30 µL. The method can include resuspending the cell suspension prior to filling the lumen of the barrel wherein resuspending comprises repeatedly pipetting the cell suspension until the cell suspension becomes uniform.

A method of implanting a viscous material (e.g., a cell suspension) into a subject in connection with a therapeutic treatment is also disclosed. The cell suspension can be a suspension of cells descendant from mesenchymal stem cells transiently-transfected by a polynucleotide encoding a Notch intracellular domain. The method can include removing a plunger of a syringe from a barrel of the syringe. The barrel can have a proximal end, a distal end, and a lumen in between the proximal end and the distal end. The method can also include filling at least part of the lumen of the barrel with the cell suspension through an opening at the proximal end and reinserting the plunger. The method can further include injecting the cell suspension into the subject using the syringe at one or more deposit sites. The method can include rotating the syringe about a longitudinal axis of the syringe prior to a subsequent injection.

The method can include aligning the barrel in a horizontal orientation prior to filling at least part of the lumen with the cells. The method can include depressing the plunger until the cell suspension fills an implantation device coupled to the syringe at the distal end of the barrel and a droplet of the cell suspension is expelled from a tip of the implantation device and discarded prior to injecting the cell suspension. The implantation device can be a needle or cannula and the tip can be a needle tip or cannula tip.

The method can include injecting from about 15 µL to about 25 µL, at least 20 µL, or 20 µL of the cell suspension at five deposit sites in the subject at an injection rate of about 5 µL per minute to about 15 µL per minute, at least 10 µL per minute, or 10 µL per minute. The method can include placing the syringe into a stereotactic frame prior to injecting the cell suspension. The method can include measuring an amount (e.g., volume) of the cell suspension injected using a meniscus of the cell suspension remaining in the barrel.

A method of treating a subject with cells is disclosed. The method can include removing a plunger of a syringe from a barrel of the syringe. The barrel has a proximal end, a distal end, and a lumen in between the proximal end and the distal end. The method can include aligning the barrel in a horizontal orientation.

The method can also include filling at least part of the lumen of the barrel with cells through an opening at the proximal end. The cell suspension can be a suspension of cells descendant from mesenchymal stem cells transiently-transfected by a polynucleotide encoding a Notch intracellular domain. Filling at least part of the lumen can include inserting a pipette tip of a micropipette into the lumen of the barrel through an opening at the proximal end and injecting the cells into the lumen using the micropipette. The method can also include reinserting a plunger tip into the lumen.

The method can further include coupling an implantation device to the syringe at the distal end of the barrel. The method can also include depressing the plunger until the cells fill the implantation device and a droplet of cells is expelled from the implantation device through a distal tip of the implantation device and discarded. The implantation device can be a cell delivery cannula or a needle.

The method can include placing the implantation device into a stabilization cannula followed by a first injection in which an amount of the cells is injected into the subject using the syringe and the implantation device at a first deposit site in the subject. The method can include rotating the syringe and/or the implantation device about a longitudinal axis of the syringe after the first injection step. The method can also include, subsequent to the first injection, retracting at least one of the syringe and the cell delivery cannula a predetermined distance followed by a second injection in which another amount of the cells is injected into the subject using the syringe and the cell delivery cannula at a second deposit site in the subject. The method can include further steps of retraction and reinjection (e.g., third, fourth, fifth, etc. injections). The predetermined distance can be between approximately 1 mm and 10 mm. The first deposit site or the second deposit site can be in the brain and/or the spinal cord of the subject.

The amount of the cells injected can be approximately 15 µL to about 25 µL, at least 20 µL, or 20 µL. The injection rate can be about 5 µL per minute to about 15 µL per minute, at least 10 µL per minute, or 10 µL per minute. The cells injected can comprise cells descendant from mesenchymal cells transiently-transfected by a polynucleotide encoding a Notch intracellular domain. The method can also include measuring a volume of the cell suspension injected using a meniscus of the cells remaining in the barrel.

Any of the methods disclosed herein can be used in connection with a therapeutic treatment to treat a traumatic brain injury. The therapeutic treatment can also be used to treat ischemic damage, retinal degeneration, neurodegenerative diseases, or a combination thereof.

DETAILED DESCRIPTION

Figure 1A:
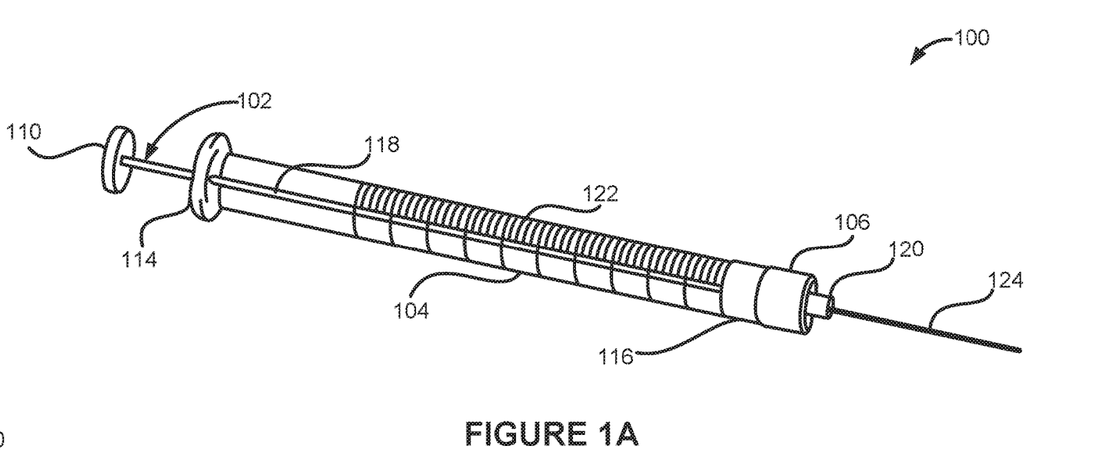
FIG. 1A illustrates a variation of a syringe for use in delivering cells.

FIG. 1A illustrates that a syringe 100 used to transplant or implant cells can include a plunger 102, a barrel 104, and a hub 106. The barrel 104 can be shaped as an elongate cylindrical tube. The barrel 104 can have a barrel proximal end 114, a barrel distal end 116, and a lumen 118 in between the barrel proximal end 114 and the barrel distal end 116. In one variation, the barrel 104 can be composed of or comprise a ceramic material such as borosilicate glass. In other variations, the barrel 104 can be composed of or comprise a polymer such as polytetrafluoroethylene (PTFE).

In one variation, the barrel 104 can have an outer diameter ranging from approximately 6.00 mm to 10.00 mm. The barrel 104 can have an inner diameter ranging from approximately 1.25 mm to 5.00 mm.

The hub 106 can be coupled to the barrel 104 at the barrel distal end 116 and comprise a mating connector 120 capable of receiving and securing a needle 124. The hub 106 can be a locking hub and can be fabricated from or comprise a polymer, a metal or metal alloy such as nickel-plated brass, or a combination thereof. The mating connector 120 can be a Luer lock connector, such as a male Luer taper, and can be composed of or comprise a polymer such as PTFE. The internal continuous bore of the mating connector 120 can be such that the needle 124 will fit tightly inside. The hub 106 can function as the interface between the syringe 100 and the needle 124.

The needle 124 can have an outer diameter ranging from approximately 0.40 mm to 0.90 mm. The needle 124 can have an inner bore diameter ranging from approximately 0.10 mm to 0.35 mm.

The wall thickness of the needle 124 can range from approximately 0.10 mm to 0.35 mm. In one variation, a Hamilton® syringe with a needle 124 ranging from 27- to 33-gauge can be used.

The tip of the needle 124 can have various point styles such as at least one of a sharp point, a beveled point, a curved point, a non-coring point, a blunt point, and a conical point. In one variation, the tip of the needle 124 can be rounded to reduce damage to brain tissue during cell implantation. In some variations, a cannula, such as the cell delivery cannula 300 of FIG. 3A, can be used instead of the needle 124.

The syringe 100 can have a total volume ranging from approximately 10 µL to 500 µL. The syringe 100 can have a dispensing volume greater than or equal to 10% of the total volume of the syringe 100. In one variation, the dispensing volume can range from approximately 1 µL to 50 µL. The syringe 100 can also include volume markings 122 or scale gradations etched or otherwise defined on an outer surface of the barrel 104. In one variation, the syringe 100 can be a Hamilton® Gastight 1700 Series syringe, such as a 100 µL Hamilton® Model 1710 TLL syringe (PN/REF: 81027).

Figure 1B:
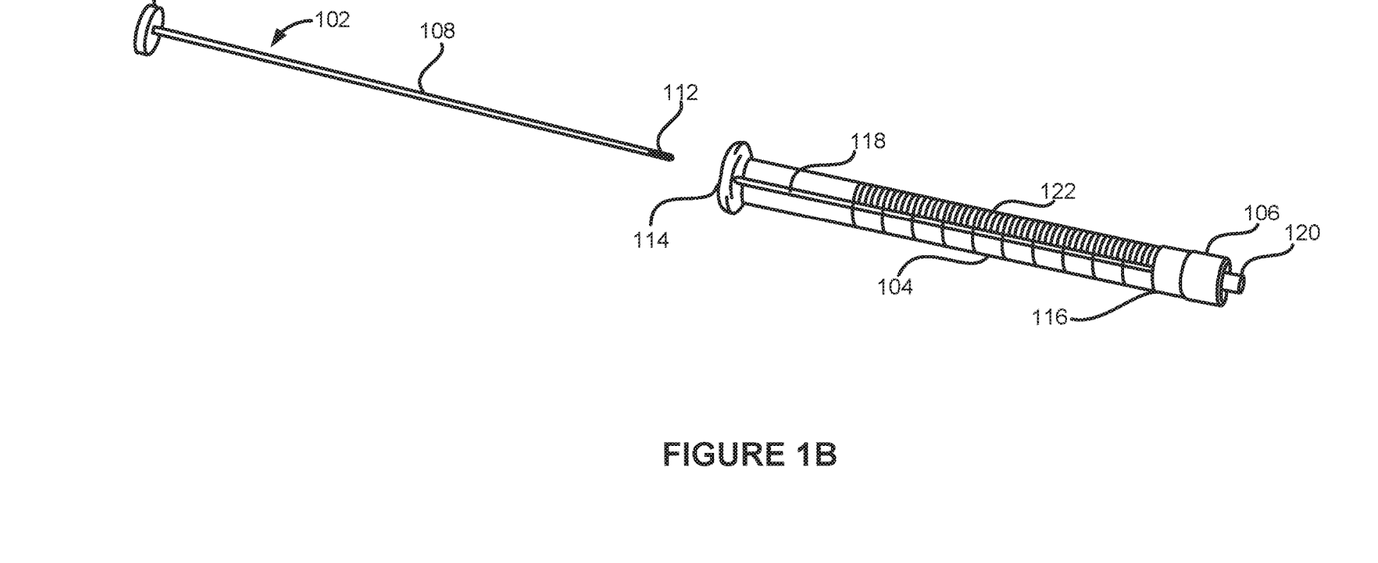
FIG. 1B illustrates a plunger of the syringe of FIG. 1A.

FIG. 1B illustrates that the plunger 102 can be removed or retracted from the barrel 104 of the syringe 100. As shown in FIG. 1B, the plunger 102 can be removed or retracted from the barrel proximal end 114. When the plunger 102 is removed or retracted from the barrel proximal end 114, the lumen 118 within the barrel 104 can be accessed through an opening at the barrel proximal end 114.

As depicted in FIG. 1B, the plunger 102 can include a plunger rod 108, a plunger head 110 attached or extending from a proximal end of the plunger rod 108, and a plunger tip 112 at a distal end of the plunger rod 108. The plunger 102 can be fabricated from or comprise a metal, a metal alloy, a polymer, a polymer composite, or a combination thereof. For example, the plunger 102 can be fabricated from or comprise stainless steel. The plunger rod 108 can be shaped as an elongate cylinder. The plunger tip 112 can be coated with a chemically inert polymeric material. The chemically inert polymeric material can include polytetrafluoroethylene (PTFE). The plunger tip 112 can be a precision-machined PTFE plunger tip. The plunger tip 112 can create a leak-free or gas-tight seal when inserted into the lumen 118 of the barrel 104. The plunger tip 112 can also remove or wipe off cellular debris from the radial surface of the lumen 118 when the plunger head 110 is depressed and the plunger tip 112 travels through the lumen 118 toward the barrel distal end 116. The lumen 118 of the syringe 100 can be designed to be substantially chemically inert by covering or coating the surface of the lumen 118 with PTFE.

Figure 2A:
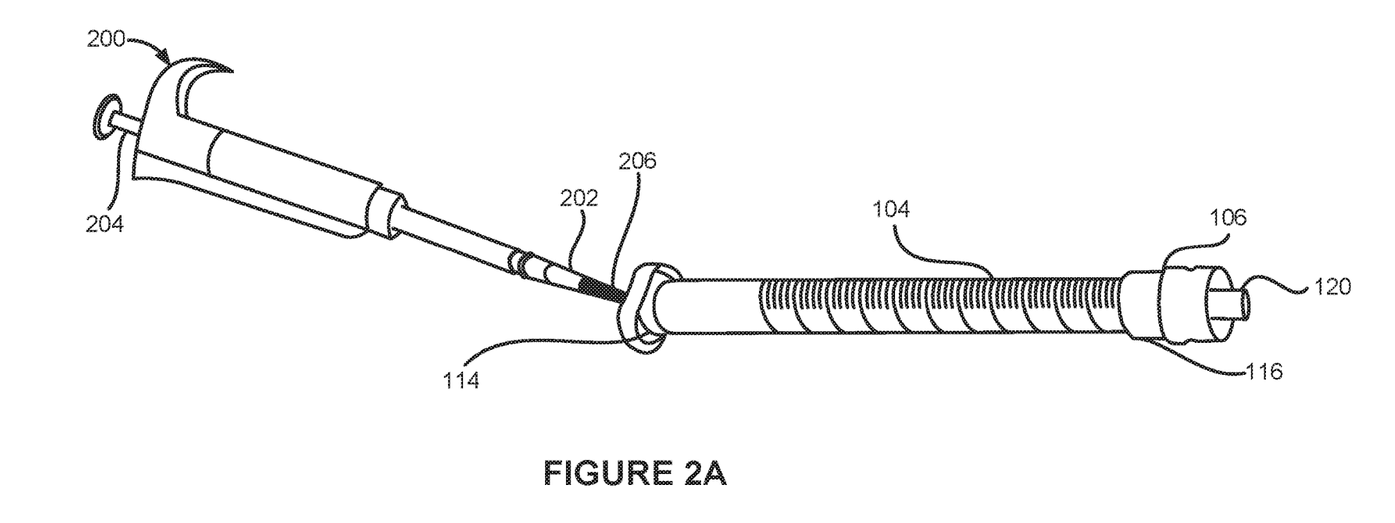
FIG. 2A illustrates a micropipette filling the syringe when the barrel of the syringe is aligned in a horizontal orientation.

FIG. 2A illustrates that the barrel 104 can be aligned in a horizontal orientation as part of a method of preparing the syringe 100 in connection with a therapeutic treatment. The method can include removing the plunger 102 of the syringe 100 from the barrel 104 and aligning the barrel 104 in the horizontal orientation. The method can further include filling the lumen 118 of the barrel 104 with a cell suspension 206 through the opening at the barrel proximal end 114.

In one variation, the cell suspension 206 can be delivered using a micropipette 200. The micropipette 200 can include a pipette tip 202 that can be inserted into the lumen 118 of the barrel 104 through an opening at the barrel proximal end 114. The pipette tip 202 can be sterile disposable plastic tips such as a VWR® Aerosol Filter Pipet Tip.

The cell suspension 206 can be loaded into the syringe 100 through the barrel proximal end 114 in connection with a cell implantation or transplantation procedure. For purposes of the present disclosure, "transplantation" and "implantation" refer to the introduction of exogenous cells into a subject. Exogenous cells can include autologous cells and allogenic cells. Autologous cells can be obtained from the subject while allogeneic cells can be obtained from an individual other than the subject.

The cell suspension 206 can include, but is not limited to, harvested cells, cultured cells, stem cells, genetically-engineered cells, or a combination thereof suspended in a buffer solution. The buffer solution can include a crystalloid solution, such as Plasma-Lyte A® from Baxter International Inc.

For example, the cell suspension 206 can include, but is not limited to, mesenchymal cells, mesenchymal stem cells (MSCs), bone marrow stromal cells (BMSCs), cells descendant from MSCs or BMSCs, cultures thereof, or a combination thereof. The cell suspension 206 or precursors thereof can be harvested from different types of connective tissue, umbilical cord blood, Wharton's jelly, adipose tissue, or dental pulp. For purposes of this disclosure, MSCs can refer to adherent, non-hematopoietic multipotent cells derived from bone marrow.

The cell suspension 206 can also contain cells descended from marrow adherent stem cells (MASCs) or human bone marrow MSCs, either of which have been transiently transfected with a vector encoding a Notch intracellular domain (NICD) (e.g., the human Notch 1 intracellular domain (NICD1)) followed by selection and subsequent culturing. Such cells can be referred to as descendants of NICD transiently-transfected MSCs or DNTT-MSCs. DNTT-MSCs can also refer to cells produced from a process comprising the steps of providing a culture of MSCs, contacting the MSC cell culture with a polynucleotide comprising sequences encoding the NCID but not encoding a full-length Notch protein, selecting cells that comprise the polynucleotide, and further culturing the selected cells in the absence of selection. For example, the selected cells can be further cultured in a standard culture medium, optionally supplemented with a serum, in the absence of any added growth factors or differentiation factors (other than those which may be present in the serum, if serum is present in the culture medium). This process produces a cell population that demonstrates superior angiogenic and neuropoietic (i.e., growth and differentiation of neural precursor cells) properties in vitro compared to their parental MSCs. The cell suspension 206 can include cells from such a cell population.

The cell suspension 206 can include cells disclosed in U.S. Pat. No. 6,989,271, issued Jan. 24, 2006, U.S. Pat. No. 7,682,825, issued Mar. 23, 2010, U.S. Pat. No. 8,361,456, issued Jan. 29, 213, U.S. Pat. No. 8,133,725, issued Mar. 13, 2012, U.S. Pat. No. 8,969,078, issued Mar. 3, 2015, U.S. Pat. No. 9,399,046, issued Jul. 26, 2016, U.S. Pat. No. 9,441,199, issued Sep. 13, 2016, U.S. Pat. No. 8,092,792, issued Jan. 10, 2012, U.S. Pat. No. 8,945,919, issued Feb. 3, 2015, U.S. Pat. No. 8,785,190, issued Jul. 22, 2014, U.S. Pat. No. 9,326,999, issued on May 3, 2016, U.S. Pat. No. 9,655,927, issued on May 23, 2017, U.S. Pat. No. 9,828,593, issued on Nov. 28, 2017, U.S. Pat. No. RE 46,382, issued on May 2, 2017, U.S. patent application Ser. No. 14/572,177, filed Dec. 16, 2014 (published as US 2015/0104435 A1), U.S. patent application Ser. No. 15/192,671, filed Jun. 24, 2016 (published as US 2016/0304835 A1), U.S. patent application Ser. No. 12/734,855, filed Aug. 23, 2010 (published as US 2010/0310529), U.S. patent application Ser. No. 14/465,344, filed Aug. 21, 2014 (published as US 2014/0363408 A1), U.S. patent application Ser. No. 12/736,665, filed Feb. 9, 2011 (published as US 2011/0136114 A1), U.S. patent application Ser. No. 13/589,849, filed Aug. 20, 2012 (published as US 2013/0210000 A1), U.S. patent application Ser. No. 15/063,290, filed Mar. 7, 2016 (published as US 2016/0263159 A1), U.S. patent application Ser. No. 13/800,585, filed Mar. 13, 2013 (published as US 2014/0186316 A1), U.S. patent application Ser. No. 14/489,934, filed Sep. 18, 2014 (published as US 2015/0197741 A1), U.S. patent application Ser. No. 14/244,685, filed on Apr. 3, 2014 (published as US 2014/0219976 A1), and U.S. patent application Ser. No. 15/076,378, filed on Mar. 21, 2016 (published as US 2016/0271181 A1), all of which are herein incorporated by reference in their entireties.

Therapeutic treatments involving the implantation or transplantation of stem cells or DNTT-MSCs can often involve the delivery or deposition of between 2 million to 10 million cells per injection. Given these dosage amounts, the cell suspension 206 can be too viscous to draw up and load through the needle 124 of the syringe 100. For example, the cell suspension 206 can clog the needle 124 when drawn up through the distal end of the needle 124. Moreover, the viability of cells drawn up through the needle 124 can be adversely affected by the shear stresses imposed on such cells. As such, loading the cell suspension 206 through the opening at the barrel proximal end 114 of the syringe 100 improves cell viability and avoids equipment malfunction.

In addition, loading the cell suspension 206 through the opening at the barrel proximal end 114 also decreases the chances that unwanted air bubbles will be injected along with the cell suspension 206. Such unwanted air bubbles can disrupt flow dynamics, clog the needle 124, and adversely affect cell viability.

The cell suspension 206 can be loaded into the syringe 100 through the barrel proximal end 114 when the barrel 104 is aligned horizontally. The barrel 104 can be aligned horizontally by being placed on a flat horizontal surface or held by a user. One benefit of aligning the barrel 104 horizontally while filling the syringe 100 is that the cells are less likely to settle toward the barrel distal end 116 and will tend to layer out evenly along the length of the barrel 104. Another benefit of aligning the barrel 104 horizontally is that the buffer solution washes over and contacts more cells in the cell suspension 206. An additional benefit of aligning the barrel 104 horizontally is that it prevents the cell suspension 206 from spilling or leaking out of the barrel 104.

Figure 2B:
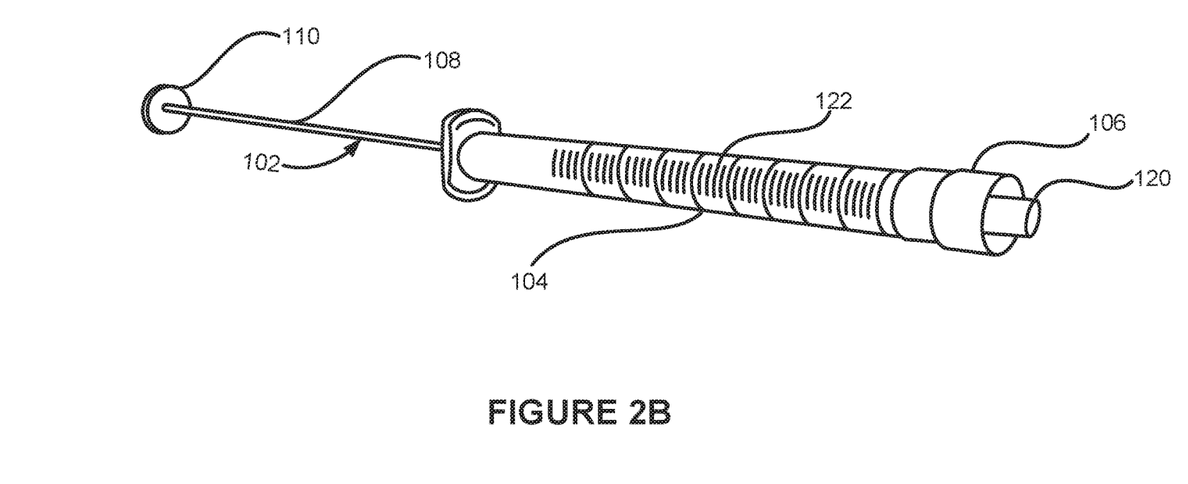
FIG. 2B illustrates a plunger being re-inserted into the syringe.

FIG. 2B illustrates that the plunger 102 can be re-inserted back into the barrel 104 through the barrel proximal end 114 after the cell suspension 206 is introduced into the lumen 118 of the barrel 104. The barrel 104 can be aligned in a horizontal orientation when the plunger 102 is re-inserted back into the barrel 104. As shown in FIG. 2B, the plunger tip 112 can be re-inserted into the lumen 118 through the barrel proximal end 114 without depressing the plunger 102 further into the barrel 104.

Figure 3A:
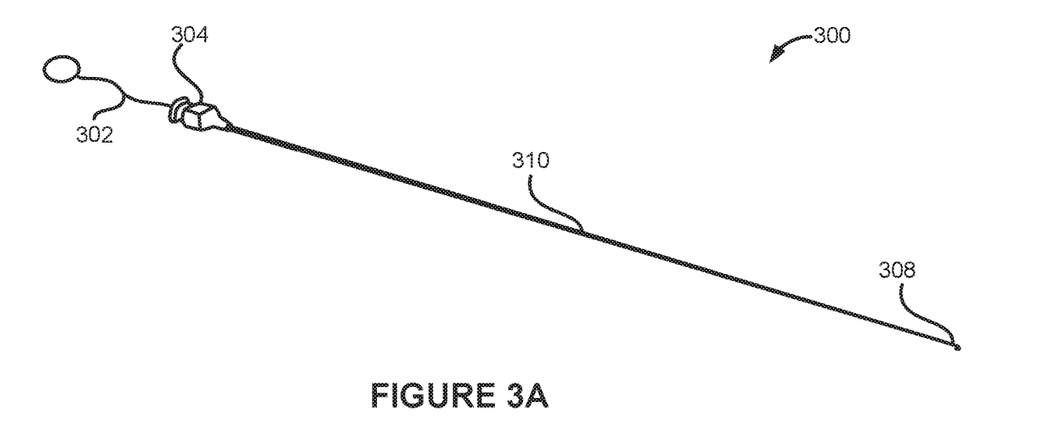
FIG. 3A illustrates a perspective view of a variation of a cell delivery cannula.

FIG. 3A illustrates that a cell delivery cannula 300 can have a cannula hub 304 configured to attach to the hub 106 of the syringe 100. The cell delivery cannula 300 can also include an inner stylet 302 that fills the internal volume of the cannula 300, a cannula rod 310, and a cannula tip 308.

The cell delivery cannula 300 can have an outer diameter of between 0.75 mm to 0.90 mm and an inner diameter of between 0.20 mm to 0.40 mm. The cell delivery cannula 300 can have a length ranging from approximately 15.0 cm to 20.0 cm.

The cell delivery cannula 300 can be composed of or comprise stainless steel such as Type 304 stainless steel. The cell delivery cannula 300 can have an internal volume ranging from approximately 15 µL to 50 µL. In one variation, the internal volume can be approximately 20 µL. The cannula rod 310 can include a lumen extending from the cannula hub 304 to the cannula tip 308.

For example, the cell delivery cannula 300 can be or include part of the Pittsburgh Cell Implantation Cannula (Synergetics® Part Number SB 2023). The inner stylet 302 can be removed from the cannula hub 304 to prepare the cell delivery cannula 300 for a cell implantation or transplantation procedure.

Figure 3B:
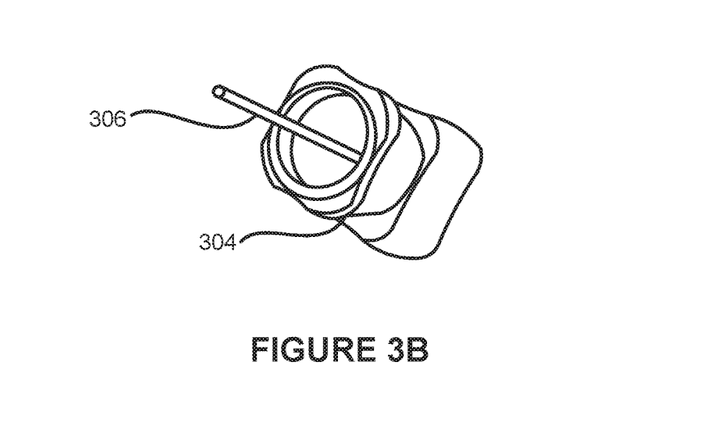
FIG. 3B illustrates a close-up perspective view of a proximal extension protruding from a hub of the cell delivery cannula of FIG. 3A.

FIG. 3B illustrates that a cannula extension 306 can be visible after removing the inner stylet 302 from the lumen of the cell delivery cannula 300. The cannula extension 306 can protrude from the cannula hub 304. The cannula extension 306 can be a rigid hollow tube in fluid communication with the lumen of the cell delivery cannula 300.

The cannula extension 306 can tightly fit into the internal bore of the mating connector 120 of the syringe 100. Once the cannula extension 306 is inserted into the bore of the mating connector 120 of the syringe 100, the cell suspension 206 can directly pass from the lumen 118 of the syringe 100 to the lumen of the cell delivery cannula 300 via the syringe hub 106, the cannula extension 306, and the cannula hub 304.

One benefit of the cannula extension 306 can include eliminating or reducing the dead space within the cannula hub 304. The dead space within a needle or cannula hub can retain significant amounts of sample from a syringe following an injection.

Figure 4A:
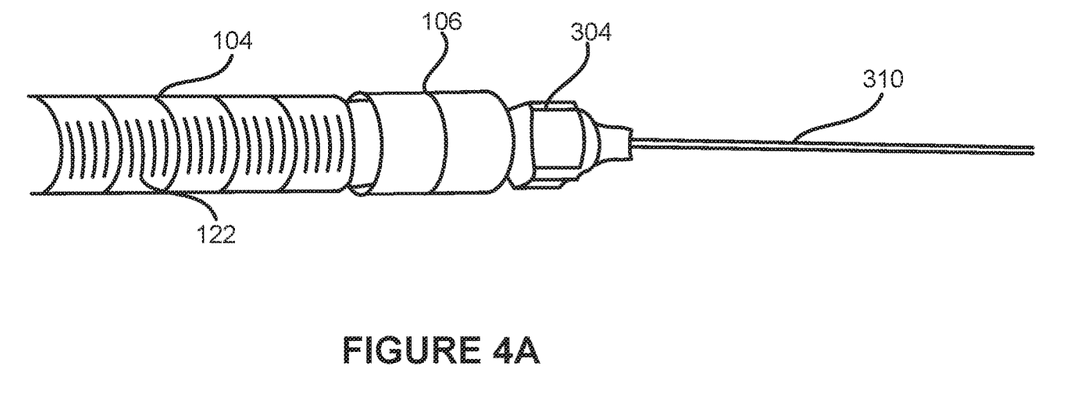
FIG. 4A illustrates a hub of a cell delivery cannula attaching to a syringe with a mating connector.

FIG. 4A illustrates that the cannula hub 304 can comprise a mating connector configured to couple to the mating connector 120. The mating connector of the cannula hub 304 can be fabricated from or comprise a polymeric material, a metal such as stainless steel or nickel-plated brass, or a combination thereof. The mating connector of the cannula hub 304 can be a Luer Lock connector, such as a female Luer fitting.

Figure 4B:
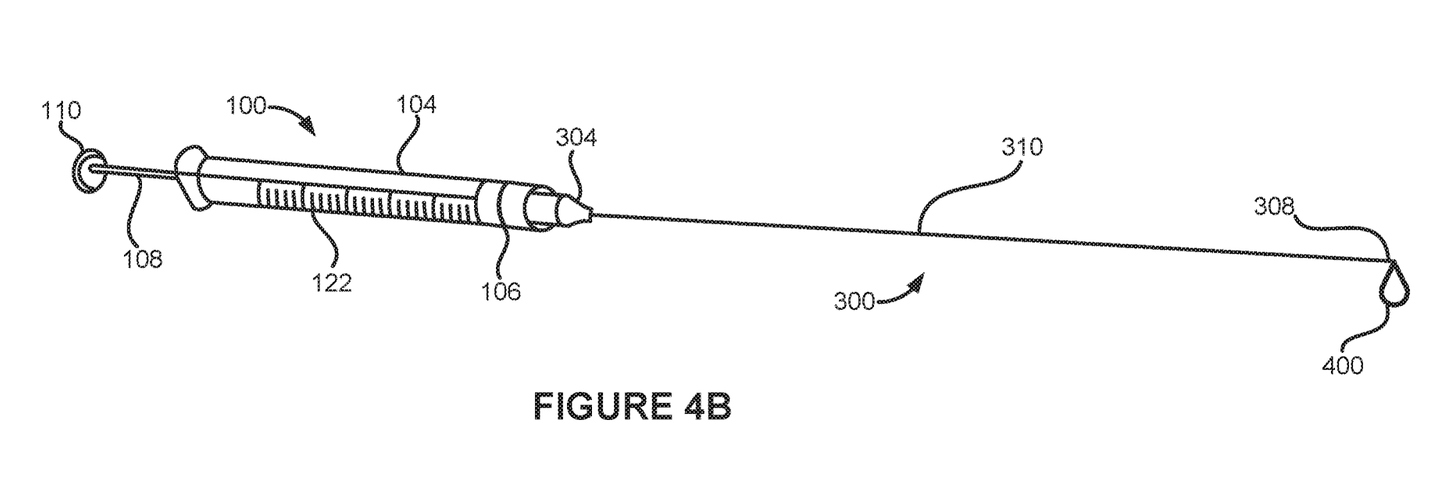
FIG. 4B illustrates a variation of a cell delivery cannula attached to a syringe.

FIG. 4B illustrates that the plunger 102 can be depressed to fill the cell delivery cannula 300 with the cell suspension 206. The plunger 102 can be depressed until a droplet 400 of the cell suspension 206 is expelled from the cell delivery cannula 300 through the cannula tip 308. Although not shown in the figures, it is contemplated by this disclosure that when the needle 124, rather than the cell delivery cannula 300, is coupled to the syringe 100, depressing the plunger 102 can also fill the needle 124 with the cell suspension 206 and a droplet 400 of the cell suspension 206 can be expelled from the needle 124.

The droplet 400 can have a volume of between 10 µL and 40 µL. For example the droplet 400 can be approximately 25 µL. The droplet 400 can be discarded prior to injecting the cell suspension 206 into the subject. Some benefits of expelling the droplet 400 of cell suspension 206 can include preventing air bubbles from being injected into the subject and eliminating dead space in the cell delivery cannula 300.

An operator of the syringe 100, such as a surgeon or an operating room technician, can use the meniscus of the cell suspension 206 in the barrel 104 and the markings 122 on the barrel 104 to determine the amount of cell suspension 206 delivered and the amount of cell suspension 206 remaining.

The cannula tip 308 of the cell delivery cannula 300 can include styles that can be configured for passage through brain tissue. For example, the cannula tip 308 can be a blunt or rounded tip. The cell delivery cannula 300 can be a cell delivery cannula as described in U.S. patent application Ser. No. 11/940,868 (published as US 2008/0132878 A1), filed Nov. 15, 2007, which is incorporated herein by reference in its entirety.

Figure 5:
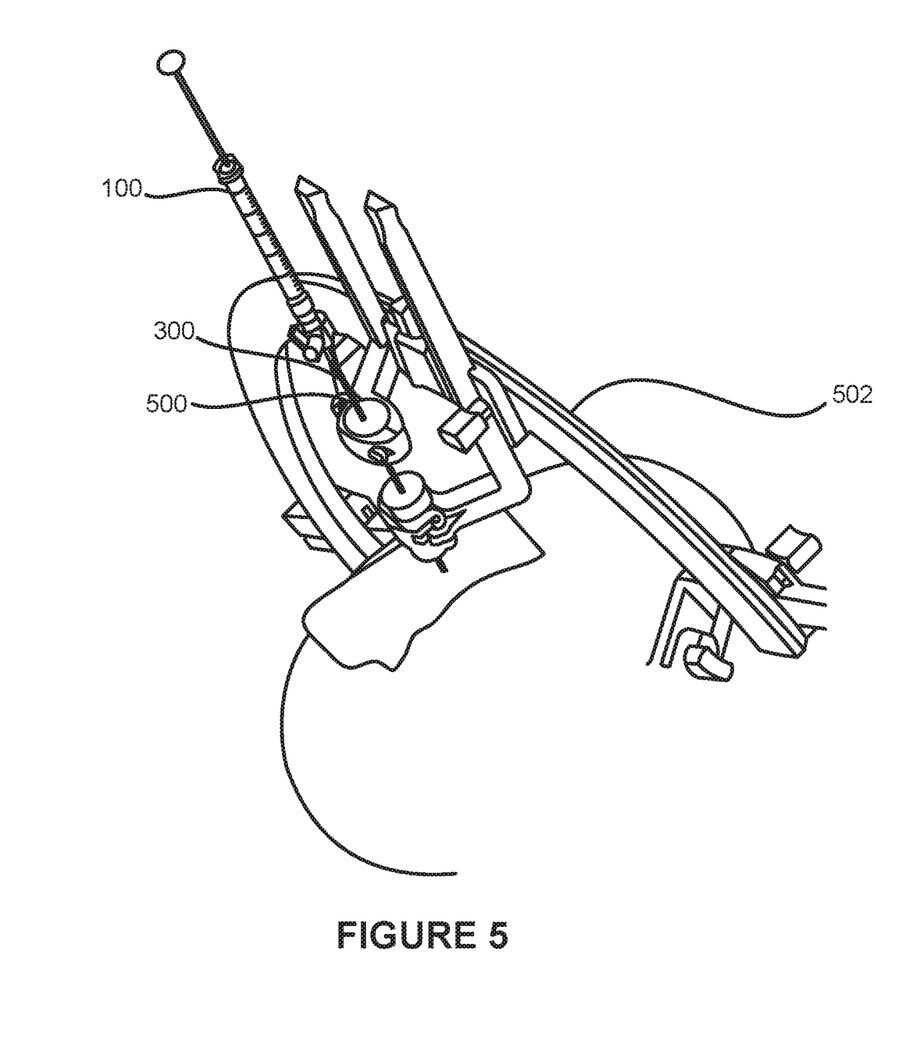
FIG. 5 illustrates a cell delivery cannula and syringe secured by a stereotactic frame and the cell delivery cannula placed inside a stabilization cannula.

FIG. 5 illustrates that the cell delivery cannula 300 can be placed inside a stabilization cannula 500 attached to a stereotactic frame 502. In one variation, the stabilization cannula 500 can include the Synergetics® SB2100 stabilization cannula (Synergetics Inc., St. Charles, Mo.). The syringe 100 can also be secured by the stereotactic frame 502 or another type of frame.

The stabilization cannula 500 can be rigid or be more rigid than the cell delivery cannula 300. The stabilization cannula 500 can have a length which is shorter than the length of the cell delivery cannula 300.

For example, the cell delivery cannula 300 can be approximately 19 cm in length. Such a length can be useful for cell implantation into brain tissue. In this example, the stabilization cannula 500 can be approximately 15 cm or 16 cm in length.

The stabilization cannula 500 can have an outer diameter ranging from approximately 0.8 mm to 2.0 mm. In one variation, the stabilization cannula 500 can have an outer diameter of approximately 1.5 mm. The stabilization cannula 400 can have an internal volume between approximately 80 µL and 120 µL.

The stabilization cannula 500 can have a two-way stopcock, a removable stylet, or a combination thereof. The removable stylet can have a diameter that is equal to the outer diameter of the cell delivery cannula 300.

The stabilization cannula 500 can be mounted in or otherwise secured by a stereotactic frame 502. In one variation, the stereotactic frame 502 can be a Leksell® model G stereotactic frame (Elekta Instruments, Atlanta, Ga.). The stereotactic frame 502 can include a stop and a guide to mount the stabilization cannula 500. In one variation, the stop can be a Leksell® Stop (Elekta Part Number 48764-10) and the guide can be a Leksell® Guide (Elekta Part Number 50150).

The stabilization cannula 500 can initially be inserted into the tissue of a subject. For example, the stabilization cannula 500 can be inserted into the subject approximately 4.00 cm to 10.0 cm from a deposit site 604 (see FIG. 6). The cell delivery cannula 300 can then be inserted into the stabilization cannula 500 and the cannula tip 308 of the cell delivery cannula 300 can protrude out of the stabilization cannula 500 and advance to either the target site 600 (see FIG. 6) or a site distal to the target site 600. The syringe 100 can be coupled to the cell delivery cannula 300 while the cell delivery cannula 300 is inserted into the stabilization cannula 400.

Figure 6:
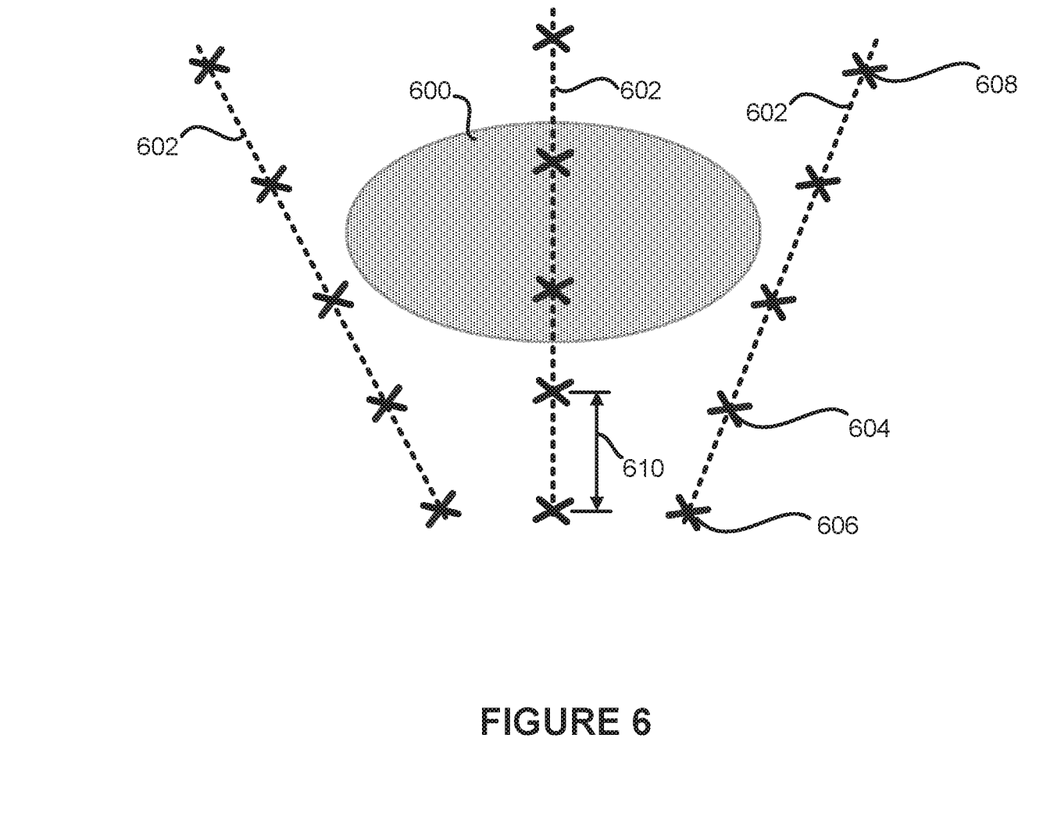
FIG. 6 illustrates a schematic of administration trajectories and deposit sites near a target site.

FIG. 6 illustrates that the cell suspension 206 can be implanted at or near a target site 600 in a subject in connection with a therapeutic treatment. The cell suspension 206 can be implanted in the subject by depositing amounts of the cell suspension 206 at or near the target site 600. The cell suspension 206 can be implanted using the syringe 100 and either the needle 124 or the cell delivery cannula 300.

The target site 600 can be a site of injury, a recommended site of administration, or any organ or tissue region within the subject. For example, when the target site 600 is a site of injury, the site of injury can differ based on the disease or condition being treated. When the disorder being treated is a central nervous system (CNS) disorder such as stroke, Parkinson's disease, or Huntington's disease, the site of injury can be a site within the basal ganglia. In the treatment of brain lesions, the site of injury can be neuronal tissue at or near the lesion. In the treatment of retinal damage, the site of injury can be the vitreous cavity or the subretinal space.

FIG. 6 shows three administration trajectories 602 in the vicinity of the target site 600. The administration trajectories 602 can be routes or pathways of administration within the subject. Each administration trajectory 602 can comprise or be defined by a plurality of deposit sites 604 including an initial deposit site 606 and a final deposit site 608. The administration trajectories 602 can be straight, curved, or a combination thereof. The administration trajectories 602 can be predetermined by a clinician or user prior to the procedure.

As shown in FIG. 6, the deposit sites 604 can be separated by a site separation distance 610. The site separation distance 610 can range from approximately 2.0 mm to 10.0 mm. For example, the site separation distance 610 can be approximately 5.0 mm. In one variation, the site separation distance 610 can be the same distance along one administration trajectory 602. In other variations, the site separation distance 610 can vary along one administration trajectory 602. The site separation distances 610 can also vary for different administration trajectories 602.

FIG. 6 also illustrates that a therapeutic treatment can involve three administration trajectories 602 surrounding a target site 600 where each of the administration trajectories 602 includes five injections of the cell suspension 206 at five deposit sites 608. For example, the cell suspension 206 can comprise stem cells or descendants of stem cells such as DNTT-MSCs and each of the administration trajectories 602 can include five deposits of 20 µL each at a rate of 10 µL per minute. A user can measure the amount of cell suspension 206 injected or deposited using the meniscus of the remaining cell suspension 206 in the barrel 104 of the syringe 100 and the markings 122 on the barrel 104.

As illustrated in FIG. 6, the initial deposit site 606 can be at a location or position distal to the target site 600. For purposes of this disclosure, distal to the target site 600 can refer to a location or position past the target site 600 which is further away from a user, such as a surgeon or medical personnel, operating or controlling the syringe 100. In other variations, the initial deposit site 606 can be at a location or position proximal to the target site 600, which is a location or position before the target site 600 which is closest to the user.

The therapeutic treatment can involve advancing the cannula tip 308 or the tip of the needle 124 to the initial deposit site 606 and injecting an amount of the cell suspension 206 at the initial deposit site 606. The cannula tip 308 or needle tip 124 can be guided using magnetic resonance imaging (MRI), ultrasound, or a combination thereof.

When the initial deposit site 606 is distal to the target site 600, the cannula tip 308 or the needle tip can be withdrawn a distance substantially equivalent to the site separation distance 610. When the cell delivery cannula 300 is used, the cannula tip 308 can be withdrawn when a user adjusts the position of the cell delivery cannula 300 relative to the stabilization cannula 500 or when a user adjusts the position of the stabilization cannula 500 relative to the stereotactic frame 502. The cannula tip 308 or the tip of the needle 124 can be retracted or pulled in a direction proximal to the initial deposit site 606.

The therapeutic treatment can also involve the user injecting another amount of the cell suspension at a subsequent deposit site 604 proximal to the initial deposit site 606. In some variations, the user can rotate the barrel 104 of the syringe 100 or both the syringe 100 and the cell delivery cannula 300 about a longitudinal axis of the syringe 100 prior to the subsequent injection. For example, the barrel 104 of the syringe 100 or both the barrel 104 of the syringe 100 and the cell delivery cannula 300 can be angularly rotated in a clockwise or counterclockwise direction. In certain variations, the rotation can be a clockwise or a counterclockwise rotation of approximately 45 degrees. In other variations, the rotation can be a clockwise or a counterclockwise of approximately 90 degrees. The syringe 100 and the cell delivery cannula 300 can be rotated to prevent the cell suspension 206 remaining in the syringe 100 and the cell delivery cannula 300 from settling or clogging.

The therapeutic treatment can involve a user withdrawing and rotating the syringe 100 or both the syringe 100 and the cell delivery cannula 300 after each injection until the tip of the needle 124 or the cannula tip 308 reaches the final deposit site 608. In one variation, the final deposit site 608 can be a location or position proximal to the target site 600. In other variations, the final deposit site 608 can be a location or position at or within the target site 600 or a location or position proximal to the initial deposit site 606 but still distal to the target site 600. In additional variations, the final deposit site 608 can be a location or position distal to the initial deposit site 606. Once a deposit or injection has been made at the final deposit site 608, the needle 124 or a combination of the cell delivery cannula 300 and the stabilization cannula 500 can be retracted out of the subject.

Although three administration trajectories 602 are shown in FIG. 6, it should be understood by one of ordinary skill in the art that the number of administration trajectories 602 and the number of deposit sites 608 can vary depending on the cells administered, the treatment protocol, and the therapeutically effective amount of cells administered for a particular treatment. As used herein, a "therapeutically effective amount" or "therapeutic amount" can refer to the number or amount of cells transplanted or implanted that reduces the severity of the symptoms associated with a particular condition or disorder. The therapeutically effective amount can vary with the type and extent of the injury as well as the overall condition of the subject.

A therapeutically effective amount of cells can refer to doses of between approximately 2.0 million cells to 30 million cells. For example, when the cells or cell suspension 206 being administered comprise stem cells or descendants of stem cells such as DNTT-MSCs, the therapeutically effective amount of cells can include any of 2.5 million cells, 5.0 million cells, or 10 million cells.

Therapeutically effective amounts of stem cells or descendants of stem cells, such as DNTT-MSCs, can be administered to injury sites to treat neurodegenerative diseases, disorders, or conditions related to the central nervous system (CNS). These diseases, disorders, or CNS conditions can include, but are not limited to, Alzheimer's disease, Parkinson's disease, Huntington's disease, amyotrophic lateral sclerosis (ALS), traumatic brain injury (TBI), stroke (ischemic and/or hemorrhagic), and spinal cord injury.

For example, DNTT-MSCs can synthesize and secrete factors that promote neuropoiesis (formation of new neurons) and angiogenesis (formation of new blood vessels). DNTT-MSCs can release biologically active fibroblast growth factors (FGF2) or basic fibroblast growth factors (bFGF). Mesenchymal cells contain large intracellular stores of FGF2 and FGF2 isoforms, which can exert neuropoietic and angiogenic effects on injured tissue sites. FGF2 can also be a potent inducer of angiogenesis and a wound healing mediator. The therapeutic effects resulting from implanting MSCs and their derivatives or descendants to injured CNS sites can be attributed, inter alia, to the secretion of soluble factors from living implanted cells, the release of soluble intracellular factors after death of implanted cells, modulation of immune function by implanted cells, production of a neurosupportive extracellular matrix by implanted cells, and formation, by implanted cells, of a pathway for migration of endogenous neurogenic cells from a neurogenic niche to the injury site.

In example treatments, approximately 2 million to 10 million DNTT-MSCs can be implanted in one implantation procedure. Such treatments can involve multiple administration trajectories 602 at or near a target site 600 with each such administration trajectory 602 including multiple deposit sites 608. Each deposit or injection at a deposit site 608 can include between approximately 10 µL and 20 µL of cell suspension 206. For example, a total of 100 µL of cell suspension 206 can be delivered per administration trajectory 602.

DNTT-MSCs can be administered as part of an allogenic cell therapy for stroke recovery, including for ischemic or hemorrhagic stroke. DNTT-MSCs can promote reperfusion of ischemic tissues in the brain. For example, transplantation of a therapeutic amount of DNTT-MSCs to a site of ischemic damage in the brain can result in new vessel growth.

Cell suspensions 206 comprising stem cells or DNTT-MSCs can also be implanted at or near a target site 600 in a subject in connection with a therapeutic treatment for traumatic brain injuries (TBI). In such treatments, the deposit sites 608 can be in an area corresponding to the peri-injured cortical area or the medial cortex. For example, DNTT-MSCs or other stem cells or derivatives thereof can be implanted within the penumbra distal or proximal to a site of injury. In addition, DNTT-MSCs or other stem cells can be implanted near motor pathways affected by the injury.

Additionally, therapeutically effective amounts of DNTT-MSCs can improve locomotor and neurological functions by forming a biological bridge between a neurogenic niche (e.g., the subventricular zone (SVZ) or the dentate gyrus) and the site of brain injury to promote rehabilitation. Transplanted DNTT-MSCs can serve as transient pathways, also known as biobridges, for long-distance migrations of host neurogenic cells from the neurogenic niche to the site of brain injury. Therapeutic amounts of DNTT-MSCs can be administered locally by a direct injection method such as an intracranial injection to treat the aforementioned conditions.

Cell suspensions 206 comprising stem cells or DNTT-MSCs can also be implanted at or near a target site 600 in an eye of the subject in connection with a therapeutic treatment for retinal degeneration. For example, DNTT-MSCs can be implanted in the eye of the subject to treat various types of retinal degenerative conditions including, but not limited to, retinitis pigmentosa (RP), age-related mascular degeneration (AMD), Usher syndrome, Stargardt's disease, choroideremia, Bardet-Biedl syndrome, Refsum disease, Best's disease, or Oguchi disease. For example, cell suspensions 206 comprising DNTT-MSCs can be administered to the eye of a subject to enhance certain photoreceptor activity or functions of the eye. Also, for example cell suspensions 206 comprising DNTT-MSCs can be administered to the eye of a subject to enhance transmission of visual signals from the retina to the visual cortex of the brain. In such treatments, cell suspensions 206 can be be transplanted into the eye of a subject directly using the needle 124 of the syringe 100. In one variation, a Hamilton® syringe with a 30-gauge needle can be used to inject DNTT-MSCs into the eye of a subject including the vitreous cavity or the subretinal space.

Figure 7A:
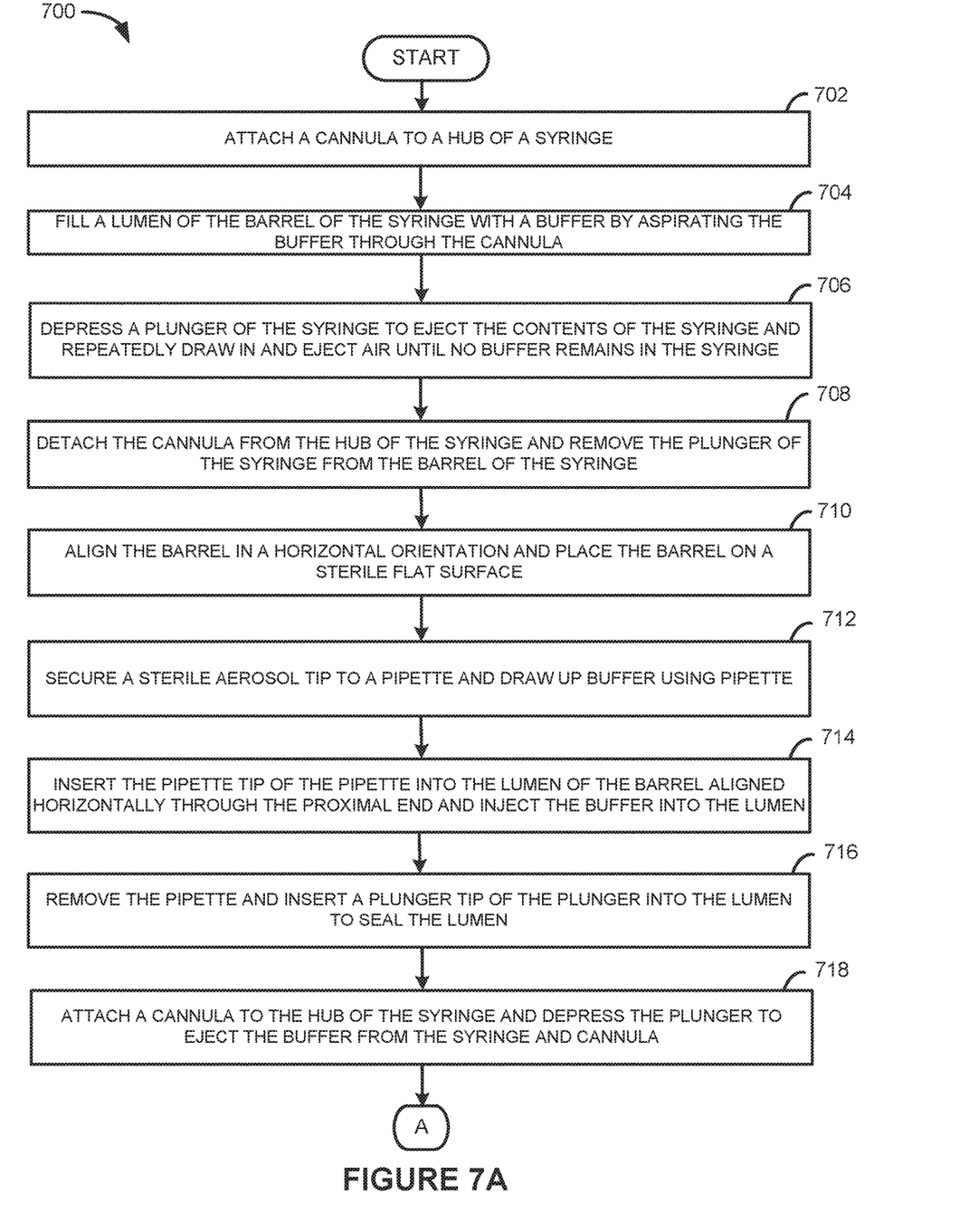
FIG. 7A illustrates a variation of a method of preparing a syringe and a cell delivery cannula for implanting cells in connection with a therapeutic treatment.

FIG. 7A illustrates a method 700 of preparing a syringe 100 and a cell delivery cannula 300 in connection with a therapeutic treatment. The method 700 can include attaching a cannula hub 304 of the cell delivery cannula 300 to a syringe hub 106 and tightening the cannula hub 304 in step 702. In one variation, the syringe 100 can be a 100 µL Hamilton® syringe and the cell delivery cannula 300 can be a Pittsburgh Cell Implantation Cannula (PIC). The method 700 can also include filling at least part of a lumen 118 of a barrel 104 of the syringe 100 with a buffer by aspirating the buffer through a cannula tip 308 of the cell delivery cannula 300 in step 704. The buffer can include Plasma-Lyte A®. The buffer can be provided in various amounts including approximately 1 mL increments.

The method 700 can also include depressing a plunger 102 of the syringe 100 to introduce or deliver buffer into the barrel 104 in step 706. Steps 704 and 706 can be repeated several times to rinse the syringe 100 and the cell delivery cannula 300. At this point, the syringe 100 attached to the cell delivery cannula 300, can be checked by the clinician or surgeon to confirm that the cell delivery cannula 300 is properly attached to the syringe 100 such that the cannula 300 is not drawing up air bubbles. After expelling the buffer, step 706 can also include repeatedly drawing in and expelling air through the cannula tip 308 until no buffer remains in the syringe 100.

The method 700 can further include detaching the cannula hub 304 from the syringe hub 106 and removing the plunger 102 from the barrel 104 of the syringe 100 in step 708. The plunger 102 and the cell delivery cannula 300 can be set aside. The method 700 can include aligning the barrel 104 in a horizontal orientation and placing the barrel 104 on a sterile flat surface in step 710. The method 700 can also include securing a sterile aerosol pipette tip 202 to a micropipette 200, and pressing down on a pipette plunger 204 to draw up buffer in step 712. The sterile aerosol pipette tip 202 can be sterile disposable plastic tips such as a VWR® Aerosol Filter pipet tip. In one variation, the micropipette 200 can be a 20-200 µL Thermo Scientific Finnpipette® micropipette. For example, the micropipette 200 can be set at 125 µL to draw up 125 µL of Plasma-Lyte A® buffer.

The method 700 can further include inserting the pipette tip 202 of the micropipette 200 into the lumen 118 of the barrel 104 aligned horizontally. The pipette tip 202 of the micropipette 200 can be inserted into the lumen 118 through the barrel proximal end 114 and buffer can be injected into the lumen 118 in step 714. The pipette tip 202 can be pressed straight into the barrel proximal end 114. The buffer can be injected slowly to prevent buffer from being expelled out of a barrel distal end 116. The method 700 can also include removing the pipette tip 202 from the barrel proximal end 114 and inserting a plunger tip 112 into the barrel proximal end 114 to seal the lumen 118 in step 716. The plunger tip 112 can be inserted just until an opening of the barrel proximal end 114 is sealed.

The method 700 can further include attaching the cannula hub 304 of the cell delivery cannula 300 to the syringe hub 106 and depressing the plunger 102 to eject the buffer from the syringe 100 and the cell delivery cannula 300 in step 718. The plunger 102 can be slowly depressed when ejecting the buffer. Further, air can also be drawn in and ejected to clear the syringe 100 and the cell delivery cannula 300 of buffer.

Figure 7B:
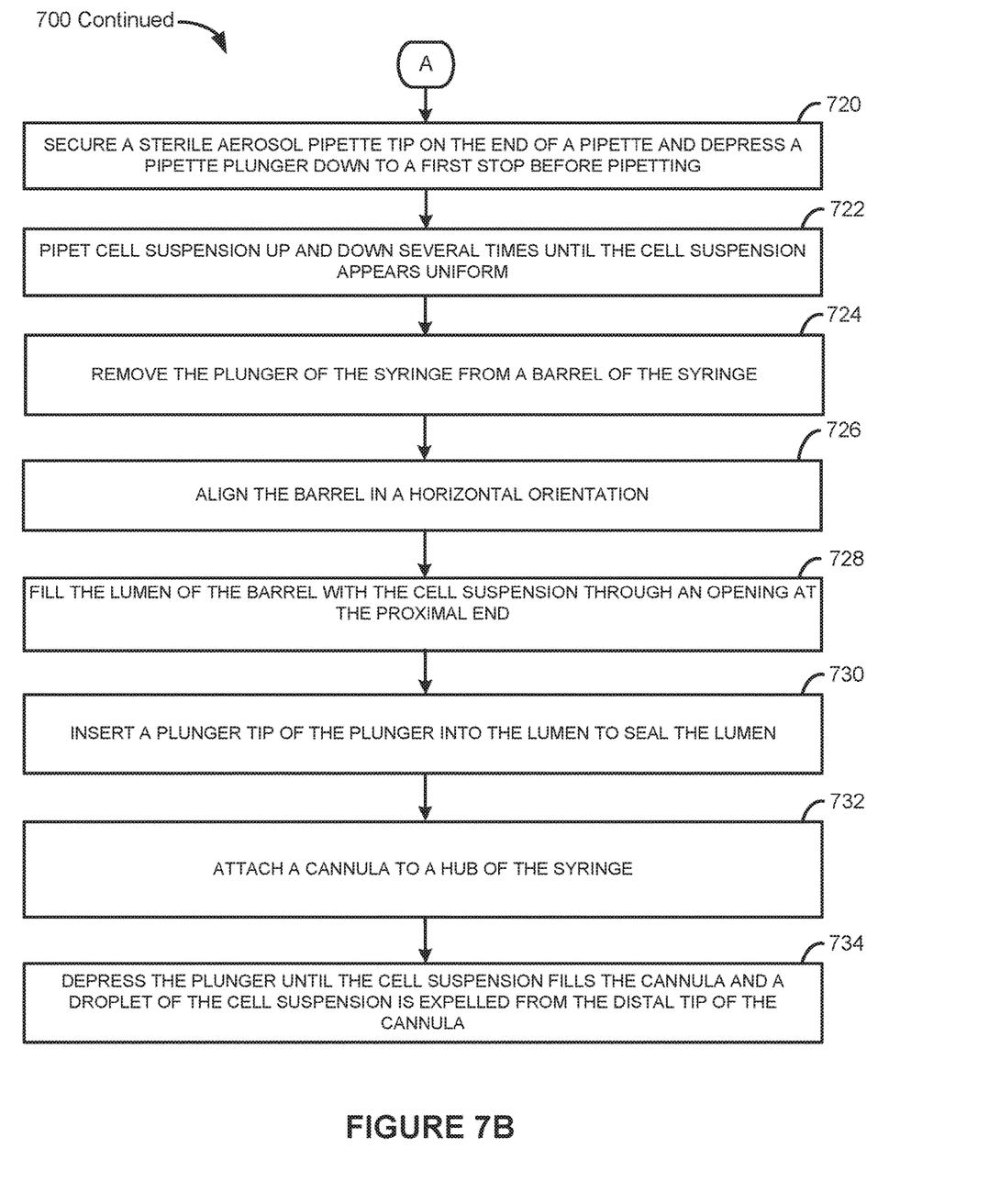
FIG. 7B illustrates additional steps in the method of preparing the syringe and the cell delivery cannula for implanting cells in connection with a therapeutic treatment.

FIG. 7B illustrates a second part of the method of preparing a syringe 100 and a cell delivery cannula 300 in connection with a therapeutic treatment. The second part of the method 700 can include securing a sterile aerosol pipette tip 202 on the end of a micropipette 200 and depressing a pipette plunger 204 down to a first stop prior to pipetting up the cell suspension 206 in step 720. For example, the micropipette 200 can be a 200 µL Thermo Scientific Finnpipette™ Micropipette. In one variation, the micropipette 200 can draw up 125 µL of cell suspension 206.

The method 700 can also include gently pipetting the cell suspension 206 up and down several times until the suspension becomes uniform in step 722. In one variation, the cell suspension 206 can include stem cells or descendants of stem cells such as DNTT-MSCs. For example, 125 µL of DNTT-MSCs can be re-suspended in step 722 by pipetting the cells up and down repeatedly using the micropipette 200. The cell suspension 206 can also be checked for bubbles.

The method 700 can further include removing a plunger 102 from the barrel 104 of the syringe 100 in step 724. The plunger 102 can be removed by pulling a portion of the plunger 102 out of the lumen 118 of the barrel 104 through the barrel proximal end 114. The method 700 can also include aligning the barrel 104 in a horizontal orientation in step 726.

The method 700 can further include filling at least part of the lumen 118 of the barrel 104 with the cell suspension 206 through the opening at the barrel proximal end 114 in step 728. The lumen 118 can be filled by inserting the pipette tip 202 of the micropipette 200 into the lumen 118 through the opening at the barrel proximal end 114 and slowly injecting the cell suspension 206 into the lumen 118.

The pipette tip 202 of the micropipette 200 can be removed from the lumen 118 through the barrel proximal end 114 after delivering the cell suspension 206 and the plunger tip 112 of the plunger 102 can be inserted into the opening of the barrel proximal end 114 to seal the lumen 118 in step 730. The plunger tip 112 can be inserted only slightly into the lumen 118 or only until the opening at the barrel proximal end 114 is sealed.

The method 700 can also include attaching the cannula hub 304 of the cell delivery cannula 300 to the syringe hub 106 and tightening the cannula hub 304 in step 732. The method 700 can further include depressing the plunger 102 until the cell suspension 206 fills the cell delivery cannula 300 and a droplet 400 of the cell suspension 206 is expelled from the cannula tip 308 in step 734. For example, when 125 µL of cell suspension 206 is initially introduced into the syringe 100, the plunger 102 can be slowly depressed until a meniscus of the cell suspension 206 is at or near the 100 µL mark of the syringe 100. In this case, the droplet 400 of cell suspension 206 expelled can be equivalent to approximately 25 µL such that approximately 100 µL of the cell suspension 206 remains in the syringe barrel 104. A piece of sterile gauze can be used to blot the droplet 400 of cell suspension 206. Although not shown in the figures, it is contemplated by this disclosure that certain steps of method 700 can also be performed by a needle 124 coupled to the syringe 100 rather than the cell delivery cannula 300 coupled to the syringe 100.

Figure 8:
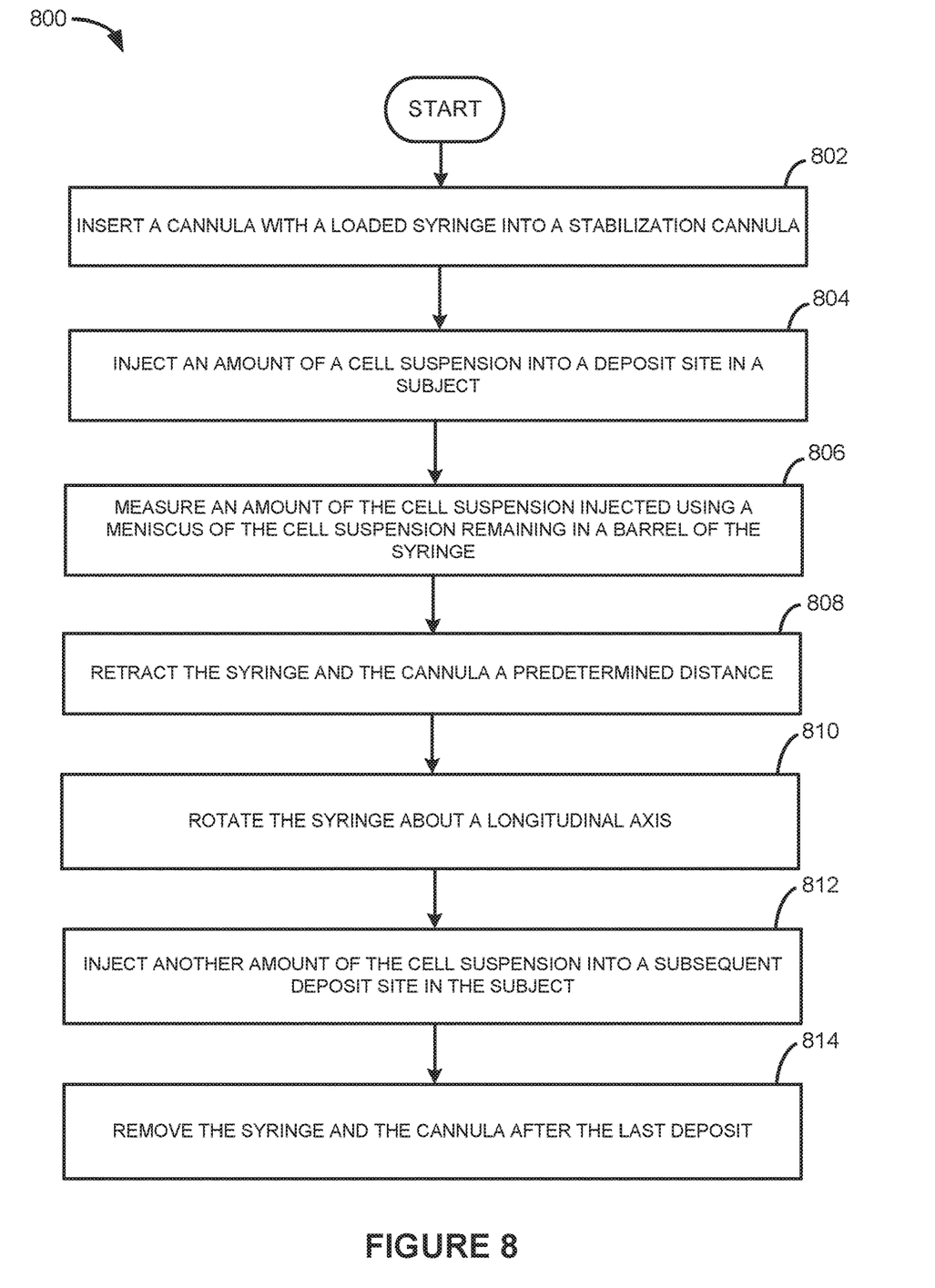
FIG. 8 illustrates a method of implanting cells as part of a therapeutic treatment.

FIG. 8 illustrates a method 800 of implanting a cell suspension 206 in a subject in connection with a therapeutic treatment. The method 800 can include inserting a cell delivery cannula 300 attached to a syringe 100 filled with cell suspension 206 (such as the cell suspension 206 from step 734 of method 700) into a stabilization cannula 500 in step 802. The stabilization cannula 500 can be mounted in a stereotactic frame 502. In one variation, the stereotactic frame 502 can be a Leksell® model G stereotactic coordinate frame (Elekta Instruments, Atlanta, Ga.). The method 800 can also include injecting an amount of the cell suspension 206 into an initial deposit site 606 of a subject in step 804. In one variation, DNTT-MSCs can be injected in five deposits of 20 µL each at a rate of 10 µL per minute along one administration trajectory 602.

The method 800 can also include measuring a volume or amount of the cell suspension 206 injected using a meniscus of the cell suspension 206 remaining in the barrel 104 of the syringe 110 in step 806. The method 800 can also include retracting the syringe 100 and the cell delivery cannula 300 a predetermined distance, such as the site separation distance 610, to a subsequent deposit site 604 after each injection in step 808. For example, the cell delivery cannula 300 can be withdrawn approximately 5.0 mm after each injection or deposit. The method 800 can also include rotating the barrel 104 of the syringe 100 (and the connected cell delivery cannula 300) about a longitudinal axis of the syringe 100 in step 810. The syringe 100 can be rotated in a clockwise or counterclockwise direction between approximately 45 degrees and 90 degrees. One benefit of rotating the syringe 100 includes preventing the cells in the cell suspension 206 from settling out of suspension.

The method 800 can further include injecting an additional amount of the cell suspension 206 into a subsequent deposit site 604 in step 812. The amount of cell suspension 206 in each deposit and the number of deposit sites can vary with each treatment. In one variation, the cell suspension 206 can be injected at a rate of 10 µL per minute and each deposit can comprise approximately 20 µL of cell suspension 206. In this variation, five deposits can be made along one administration trajectory 602 for a total deposit of 100 µL. The implantation time can range from approximately 50 minutes to 70 minutes with a maximum allowable time of 180 minutes from cell preparation to final implantation.

The method 800 can also include removing the cell delivery cannula 300 from the stabilization cannula 500 after injecting the cell suspension 206 in the final deposit site 608 in step 814. After the last deposit at the final deposit site 608, the cell delivery system can be prepared for additional implantations. A vial of buffer such as Plasma-Lyte A can be used to rinse the cell delivery system (including the syringe 100 and the cell delivery cannula 300) by the procedure described in method 700 (see FIG. 7A). Additional cell suspensions 206 can be provided from a second vial or aliquot of cells and re-suspended in accordance with step 722 of method 700 (see FIG. 7B). The stabilization cannula 500 can be re-positioned for the next administration trajectory 602. The syringe 100 and the cell delivery cannula 300 can be filled with the additional cell suspension 206 using the procedure described in method 700. The methods and steps can be repeated as needed depending on the number of administration trajectories 602.

The methods described herein are effective in delivering viscous cell suspensions, such as stem cells or stem cell derivatives such as DNTT-MSCs, to a patient as part of a therapeutic treatment. The flowcharts depicted in FIGS. 7A, 7B, and 8 do not require the particular order shown to achieve the desired result and certain steps may occur in parallel, be omitted, or a combination thereof.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts depicted in the figures do not require the particular order shown to achieve the desired result. Moreover, additional steps or operations may be provided or steps or operations may be eliminated to achieve the desired result.

Where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, and patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

I claim:

1. A method of implanting a viscous material into a subject in connection with a therapeutic treatment, the method comprising:
   removing a plunger of a syringe from a barrel of the syringe, wherein the barrel has a proximal end, a distal end, and a lumen in between the proximal end and the distal end;
   filling at least part of the lumen with the viscous material through an opening at the proximal end and reinserting the plunger;
   coupling a needle or a cannula to the distal end of the barrel of the syringe;
   injecting the viscous material into the subject using the syringe at one or more deposit sites; and
   rotating the syringe about a longitudinal axis of the syringe after each injection.

2. The method of claim 1, wherein, for injections at more than one deposit site, the method further comprises rotating the syringe about a longitudinal axis of the syringe after each injection.

3. The method of claim 1, further comprising aligning the barrel in a horizontal orientation prior to filling at least part of the lumen with the viscous material.

4. The method of claim 1, further comprising depressing the plunger until the viscous material fills the needle coupled to the syringe at the distal end of the barrel and a droplet of the viscous material is expelled from the needle through a needle tip and discarded prior to injecting the viscous material.

5. The method of claim 1, wherein the injecting of the viscous material comprises injecting at least 20 µL of the viscous material at each of five deposit sites in the subject at an injection rate of at least 10 µL per minute.

6. The method of claim 1, further comprising placing the syringe into a stereotactic frame prior to injecting the viscous material.

7. The method of claim 1, further comprising measuring a volume of the viscous material injected using a meniscus of the viscous material remaining in the barrel.

8. The method of claim 1, wherein the therapeutic treatment comprises at least one of treatment of a traumatic brain injury, treatment of ischemic damage, treatment of retinal degeneration, and treatment of a neurodegenerative disease.

9. The method of claim 1, wherein the viscous material is a cell suspension.

10. The method of claim 9, wherein the cell suspension comprises cells descendant from mesenchymal stem cells transiently-transfected by a polynucleotide encoding a Notch intracellular domain.

11. A method of treating a subject with cells, the method comprising:

removing a plunger of a syringe from a barrel of the syringe, wherein the barrel has a proximal end, a distal end, and a lumen in between the proximal end and the distal end;

filling at least part of the lumen with the cells through an opening at the proximal end and reinserting the plunger;

coupling an implantation device to the syringe at the distal end of the barrel;

injecting an amount of the cells into the subject using the syringe and the implantation device at a first deposit site in the subject;

rotating at least one of the syringe and the implantation device about a longitudinal axis; and injecting another amount of the cells into the subject using the syringe and the implantation device at a second deposit site in the subject.

12. The method of claim 11, further comprising aligning the barrel in a horizontal orientation prior to filling at least part of the lumen with the cells.

13. The method of claim 11, further comprising depressing the plunger until the cells fill the implantation device and a droplet of the cells is expelled from the implantation device through a distal tip of the implantation device and discarded prior to injecting the cells.

14. The method of claim 11, further comprising retracting at least one of the syringe and the implantation device a predetermined distance subsequent to injecting at the first deposit site and prior to injecting the cells at the second deposit site.

15. The method of claim 14, wherein the predetermined distance is between 1 mm and 10 mm, and wherein at least one of the first deposit site and the second deposit site is in the brain of the subject.

16. The method of claim 11, further comprising placing the implantation device into a stabilization cannula prior to injecting the cells.

17. The method of claim 11, further comprising measuring an amount of the cells injected using a meniscus of the cells remaining in the barrel.

18. The method of claim 11, wherein filling at least part of the lumen comprises inserting a pipette tip of a micropipette into the lumen of the barrel through an opening at the proximal end when the barrel is aligned in the horizontal orientation and injecting the cells into the lumen using the micropipette.

19. The method of claim 11, wherein the amount of the cells injected at each deposit site is 20 μL.

20. The method of claim 11, wherein the cells comprise cells descendant from mesenchymal stem cells transiently-transfected by a polynucleotide encoding a Notch intracellular domain.

21. The method of claim 11, wherein the implantation device is at least one of a cannula and a needle.

22. The method of claim 11, wherein the implantation device is a cannula, wherein the cannula comprises a proximal end and a distal end, wherein the proximal end comprises a cannula hub, wherein the cannula hub comprises a cannula extension that is in fluid communication with the lumen of the cannula and that protrudes from the cannula hub so that it extends into the lumen of the syringe at a distal end of the syringe.

* * * * *